(12) United States Patent
Pollari et al.

(10) Patent No.: US 11,779,289 B2
(45) Date of Patent: Oct. 10, 2023

(54) TWO-WAY MIRROR DISPLAY FOR DENTAL TREATMENT SYSTEM

(71) Applicant: PaloDEx Group OY, Tuusula (FI)

(72) Inventors: Mika Pollari, Vantaa (FI); Tuomas Alhonnoro, Espoo (FI); Ville Inkiläinen, Helsinki (FI); Maaria Rantala, Espoo (FI); Lauri Harhanen, Masala (FI); Jorma Savolainen, Helsinki (FI); Ari Metso, Jokela (FI)

(73) Assignee: PaloDEx Group OY, Tuusula (FI)

( * ) Notice: Subject to any disclaimer, the term of this patent is extended or adjusted under 35 U.S.C. 154(b) by 189 days.

(21) Appl. No.: 17/088,281

(22) Filed: Nov. 3, 2020

(65) Prior Publication Data

US 2022/0138934 A1    May 5, 2022

(51) Int. Cl.
| | |
|---|---|
| *A61B 6/00* | (2006.01) |
| *A61B 6/04* | (2006.01) |
| *G06T 7/70* | (2017.01) |
| *A61B 6/14* | (2006.01) |
| *A61B 90/00* | (2016.01) |

(52) U.S. Cl.
CPC ............. *A61B 6/04* (2013.01); *A61B 6/14* (2013.01); *A61B 6/461* (2013.01); *A61B 6/467* (2013.01); *A61B 6/488* (2013.01); *G06T 7/70* (2017.01); *A61B 2090/365* (2016.02); *G06T 2207/30201* (2013.01)

(58) Field of Classification Search
None
See application file for complete search history.

(56) References Cited

U.S. PATENT DOCUMENTS

| | | | | |
|---|---|---|---|---|
| 2018/0279883 | A1* | 10/2018 | Navab | A61B 6/5247 |
| 2019/0357861 | A1 | 11/2019 | Varlet | |

FOREIGN PATENT DOCUMENTS

| | | |
|---|---|---|
| EP | 2113200 A1 | 11/2009 |
| EP | 3103395 A1 | 12/2016 |
| KR | 20070025045 A | 3/2007 |
| KR | 100707790 B1 | 4/2007 |
| WO | 2017108703 A1 | 6/2017 |

OTHER PUBLICATIONS

International Search Report and Written Opinion for Application No. PCT/EP2021/080333 dated Feb. 14, 2022 (14 pages).

* cited by examiner

*Primary Examiner* — Hoon K Song
(74) *Attorney, Agent, or Firm* — Michael Best & Friedrich LLP (57) ABSTRACT

Systems and methods utilizing a two-way mirror display for patient self-positioning for dental x-ray image acquisition. The system includes a camera configured to capture an image of a patient, a display, a two-way mirror positioned between a patient location and the display, and an electronic processor. The electronic processor is configured to select, based upon a user input, an operating mode for the display; and based upon the selected operating mode, displaying at least one image on the display. The method includes receiving image data from a camera, identifying at least one facial feature of the patient in the image data, determining if a face of the patient is aligned with at least one anatomical plane based upon the at least one facial feature, and displaying at least one movement guide on a display based upon the determined alignment of the face of the patient.

14 Claims, 8 Drawing Sheets

TWO-WAY MIRROR DISPLAY FOR DENTAL TREATMENT SYSTEM

BACKGROUND OF THE INVENTION

Many dental procedures involve a patient's teeth being imaged by a camera or other image acquisition device, for example, an x-ray or optical scanner or camera. The imaging results in the generation of images. Depending on the type of image acquisition device used and the procedure performed, patients may be standing, sitting, or lying down on a treatment table during x-ray image acquisition.

X-ray image acquisition procedures can be difficult to complete. In many cases, precise and still positioning of the patient is needed to capture high-quality and accurate images of an anatomical region of interest. Patient movement can result in capturing images of areas other than a desired anatomical region of interest. Patient movement may result in degraded image quality. Shaking, rocking, talking, or other patient movement may result in blurred or otherwise low-quality images. In some cases, a patient may become fearful, agitated, or tired. A patient may move back and forth, move out of a desired patient position, or not hold a desired position long enough for x-ray image acquisition to complete. In some cases, the patient may feel isolated and feel that he or she is receiving inadequate feedback from a dentist or dental technician regarding the image of acquisition or the position of the patient. Thus, a dentist or dental technician must often attempt to precisely position patients while also managing their patients' anxiety and desire for human communication while x-ray image acquisition is taking place.

SUMMARY

Therefore, a system is needed to assist in positioning the patient for proper x-ray image acquisition. By properly positioning the patient and aiding in maintaining the proper position throughout the x-ray image acquisition procedure, images with better image quality and less positioning error image artefacts can be produced. Better images lead to faster, more accurate treatment planning, reduce the need for repeated image acquisitions, and increase x-ray image acquisition efficiency and throughput for a dental facility.

Among other things, embodiments systems described herein help to correct for inexperienced system operators, for example, new dental technicians, who may not be fully trained in the operation of dental x-ray image acquisition systems. By providing self-positioning guidance to the patient, the operator's inexperience is reduced as a factor in acquiring high quality images.

Patient satisfaction is also increased. In some embodiments, the patient has an active role in self-positioning for x-ray image acquisition. Self-positioning may result in a more relaxed and engaged patient during the imaging procedure, which leads to less patient-induced error in the images produced during the procedure. In addition, some embodiments provide patient-specific workflows in order to accommodate specific patient needs. In one example, patients with bad eyesight or hearing are provided with larger graphics or more text to aid in self-positioning for the image acquisition procedure. In another example, a patient that only speaks one language is provided with instructions in their native language to better facilitate communication with the patient.

One embodiment provides a dental x-ray image acquisition system. The system includes at least one camera configured to capture an image of a patient, a display configured to display an image, a two-way mirror positioned in between a patient location and the display, and an electronic processor coupled to the camera and the display, the electronic processor configured to control the display and the camera.

Another embodiment provides a dental x-ray image acquisition system. The system includes a camera configured to capture an image of a patient, a display, a two-way mirror positioned in between a patient location and the display, and an electronic processor coupled to the camera and the display, the electronic processor configured to select, based upon a user input, an operating mode for the display and, based upon the selected operating mode, display at least one image on the display.

A further embodiment provides a method for positioning a patient for x-ray image acquisition. The method includes receiving, with an electronic processor, image data from a camera; identifying, with the electronic processor, at least one facial feature of the patient in the image data; determining, with the electronic processor, if a face of the patient is aligned with at least one anatomical plane based upon the at least one facial feature; and displaying, with the electronic processor, at least one movement guide on a display based upon the determined alignment of the face of the patient.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

For ease of description, some or all of the example systems presented herein are illustrated with a single example of each of its component parts. Some examples may not describe or illustrate all components of the systems. Other example embodiments may include more or fewer of each of the illustrated components, may combine some components, or may include additional or alternative components.

Figure 1A:
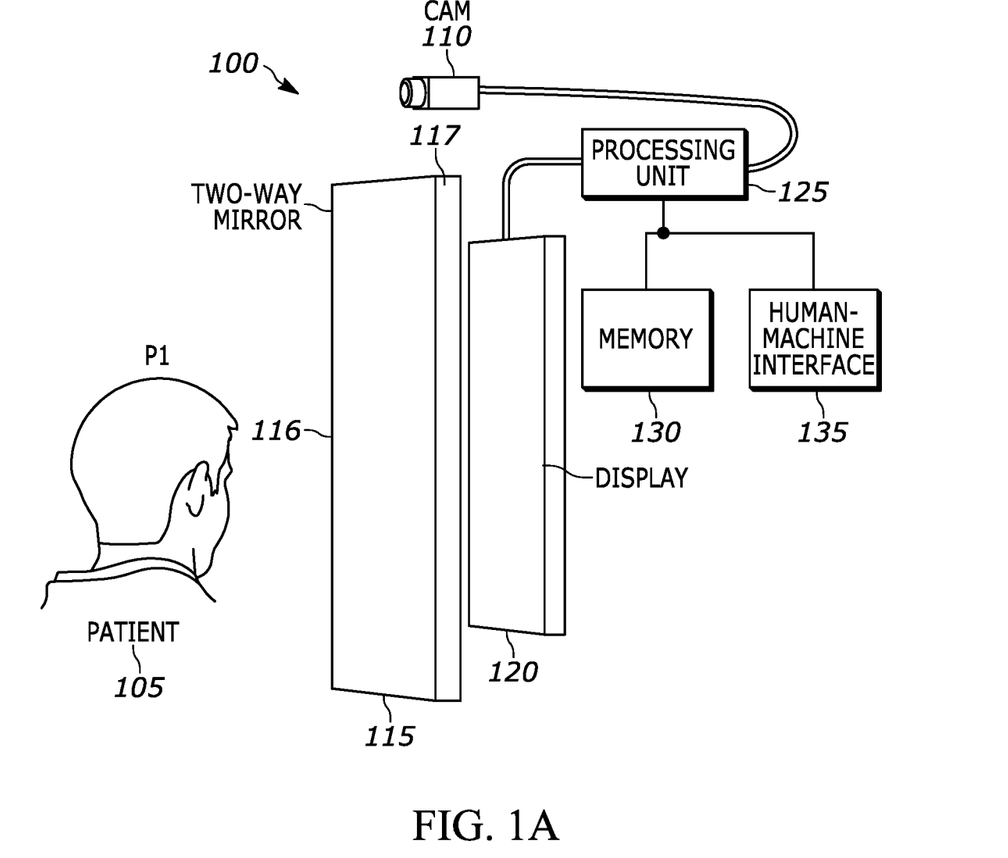
FIG. 1A illustrates a system for imaging a patient according to one embodiment.

FIG. 1 illustrates a system 100 for imaging a patient 105 located at a patient location P1 according to one embodiment. The system 100 includes at least one camera 110, a two-way mirror 115, and a display 120. The two-way mirror 115 is positioned in between the patient location P1 and the display 120. The system 100 also includes an electronic processor 125, a non-transitory computer-readable memory 130, and a human-machine interface 135. As its name implies, the two-way mirror 115 appears reflective on one side and transparent at the other. As is explained in greater detail below, the perception of one-way transmission is achieved when one side of the mirror is brightly lit and the other side is dark. This allows viewing from the darkened side but not from the brightly lit side.

Figure 1B:
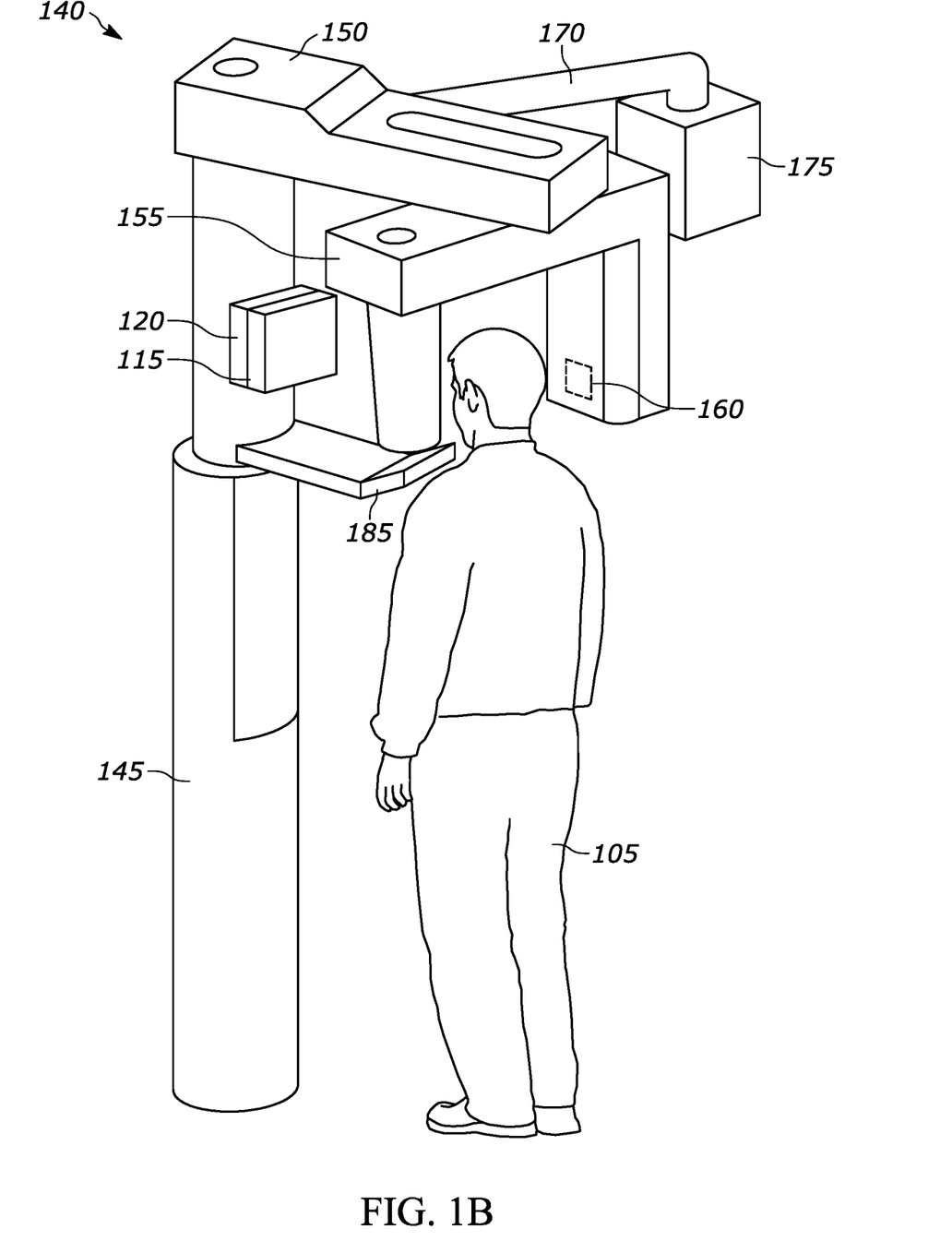
FIG. 1B illustrates an x-ray imaging system according to one embodiment.
Figure 1C:
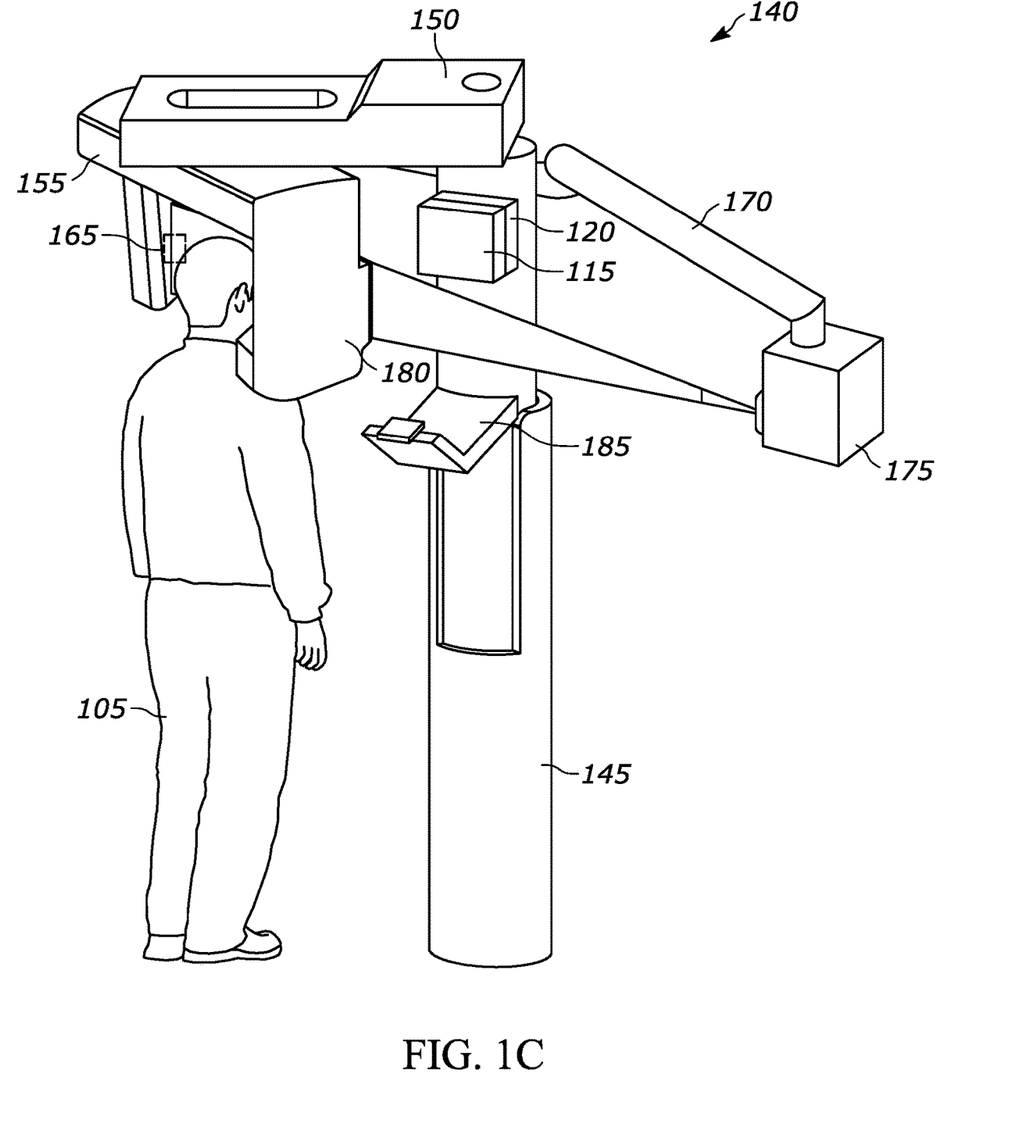
FIG. 1C illustrates an x-ray imaging system according to one embodiment.

In some embodiments, the system 100 for imaging a patient 105 is coupled to or otherwise implemented with an X-ray imaging system. An example of an X-ray imaging system 140 is illustrated in FIGS. 1B and 1C. The X-ray imaging system 140 includes a column 145 that extends vertically, for example, from a frame or ground surface. In some embodiments, the column 145 is vertically adjustable (for example, in a telescoping manner).

The X-ray imaging system 140 additionally includes an upper shelf 150 (for example, arm or top support member) that can be rotatably coupled to the column 145 generally at an upper end of the column 145 or fixed at a particular point on the column 145. In the illustrated embodiment, the upper shelf 150 is oriented along a direction that is perpendicular (for example, horizontal) to the column 145. In other embodiments, the X-ray imaging system 140 includes a housing coupled to the column, and the upper shelf is instead rotatably coupled to the housing.

With continued reference to FIGS. 1B and 1C, the X-ray imaging system 140 additionally includes a rotating part 155 (for example, arm or gantry arm) that is coupled to the upper shelf 150. The illustrated rotating part 155 is generally C-shaped, although other embodiments include other shapes. The rotating part 155 includes an X-ray source 160 (illustrated schematically in FIG. 1B) at one end of the rotating part 155, and a detector unit 165 (illustrated schematically in both FIG. 1B and FIG. 1C) at an opposite end of the rotating part 155, such that a head of the patient 105 can be positioned therebetween to produce (for example, provide data for) a panoramic, computed tomography, or cephalometric image. For example, FIG. 1B illustrates an example of a panoramic or computed tomography imaging, while FIG. 1C illustrates an example of a cephalometric imaging.

In some embodiments, the X-ray imaging system 140 additionally includes at least one cephalometric arm 170 coupled (for example, rotationally coupled) to the column 145. The cephalometric arm 170 has a distal end having a second X-ray source 175 for use in the cephalometric imaging. As illustrated in FIG. 1C, the rotating part 155 includes a collimator 180, such that when the second X-ray source 175 is activated, an X-ray beam is sent through the collimator 180 to the detector unit 165. In some embodiments where there are two X-ray sources (X-ray source 160 and X-ray source 175), the upper shelf 150 may optionally pivot via the rotating part 155, but it is not necessary for the upper shelf 150 to be able to pivot, and instead the upper shelf 150 may be in a fixed location. In other embodiments, two X-ray sources are not used. In these embodiments, the X-ray source 160 is used, for example, for CT, panoramic imaging, and cephalometric imaging. In some embodiments, CT image data gathered from the X-ray source 160 may be used to synthesize cephalometric images.

With continued reference to FIGS. 1B and 1C, in the illustrated embodiment the X-ray imaging system 140 additionally includes a lower shelf 185 coupled to the column 145. In some embodiments, the lower shelf 185 is fixed to the column 145, whereas in other embodiments the lower shelf rotationally coupled to the column 145. The lower shelf 185 provides added support for the head (for example, chin) of the patient 105. Other embodiments do not include a lower shelf, or include a lower shelf other than that illustrated.

While not illustrated, in some embodiments the X-ray imaging system 140 includes an additional arm or arms having a further patient support structure (for example, ear or nose supports) for supporting the patient's head during cephalometric imaging, and/or includes a chair such that the patient may instead be seated (as opposed to standing) during one or more of the panoramic, computed tomography, or cephalometric imaging.

With continued reference to FIGS. 1B and 1C, at least one of the camera 110, the two-way mirror 115, and the display 120 is coupled (for example, rigidly attached or rotationally coupled) to the column 145 or to another component of the X-ray imaging system 140 (for example, the upper shelf 150 or the rotating part 155). In the illustrated embodiment, the display 120 (which is illustrated schematically and includes the camera 110) is fixed to the column 145. The two-way mirror 115 (also illustrated schematically) is fixed in place in front of the display 120, such that the display is positioned between the outside of the column 145 and the two-way mirror 115. In some embodiments, fasteners or other structures are used to secure the display 120 and/or two-way mirror 115 in place. In some embodiments, the display 120 and/or two-way mirror 115 are integrated into the column 145 itself. In yet other embodiments, the display and/or two-way mirror 115 are spaced from the column 145. For example, in some embodiments the display 120 and/or two-way mirror 115 are coupled to their own separate column that is spaced away from the column 145, and that extends from a frame or ground surface similar to the column 145.

During use, and as described further below, the two-way mirror 115 is positioned in front of a face of the patient 105 to help align the patient 105 for imaging by the X-ray imaging system 140.

Returning to FIG. 1A, the camera 110 is used for capturing image data of the patient 105. In some embodiments, the camera 110 may be located above the two-way mirror 115. In other embodiments, the camera 110 may be located behind the two-way mirror 115 and is configured to capture images through the two-way mirror 115. The camera 110 may also be a three-dimensional ("3-D") camera. A 3-D camera may be a stereo camera or a multi-camera setup based on stereo triangulation or a camera with a stereo lens.

A 3-D camera may also be a range camera operating according to any range imaging technique, for example stereo triangulation, sheet of light triangulation, structured light, time-of-flight, interferometry, coded aperture or any other range imaging technique.

The two-way mirror 115 reflects and transmits light through both sides of the two-way mirror 115. The brighter side of the two-way mirror dictates what a user of the two-way mirror 115 sees. For example, if the patient is looking at a patient side surface 116 of the two-way mirror 115 and light on the patient side surface 116 is brighter than light on a display side surface 117, the patient 105 sees the two-way mirror 115 as a regular mirror reflecting the patient 105. In contrast, if light on the display side surface 117 is brighter than light on the patient side surface 116, the patient is able to see through the two-way mirror 115 to observe objects on the display side surface 117, for example, the display 120.

The display 120 may be, for example, a computer monitor, tablet computer, or other electronic display that is configured to display, for example, images, user interfaces, alignment lines, and other visual objects to the patient 105. Assuming that illumination conditions in a patient environment (e.g., a dental practice room) remain constant, the brightness of the display 120 controls what the patient 105 views in or through the two-way mirror 115.

Figure 2:
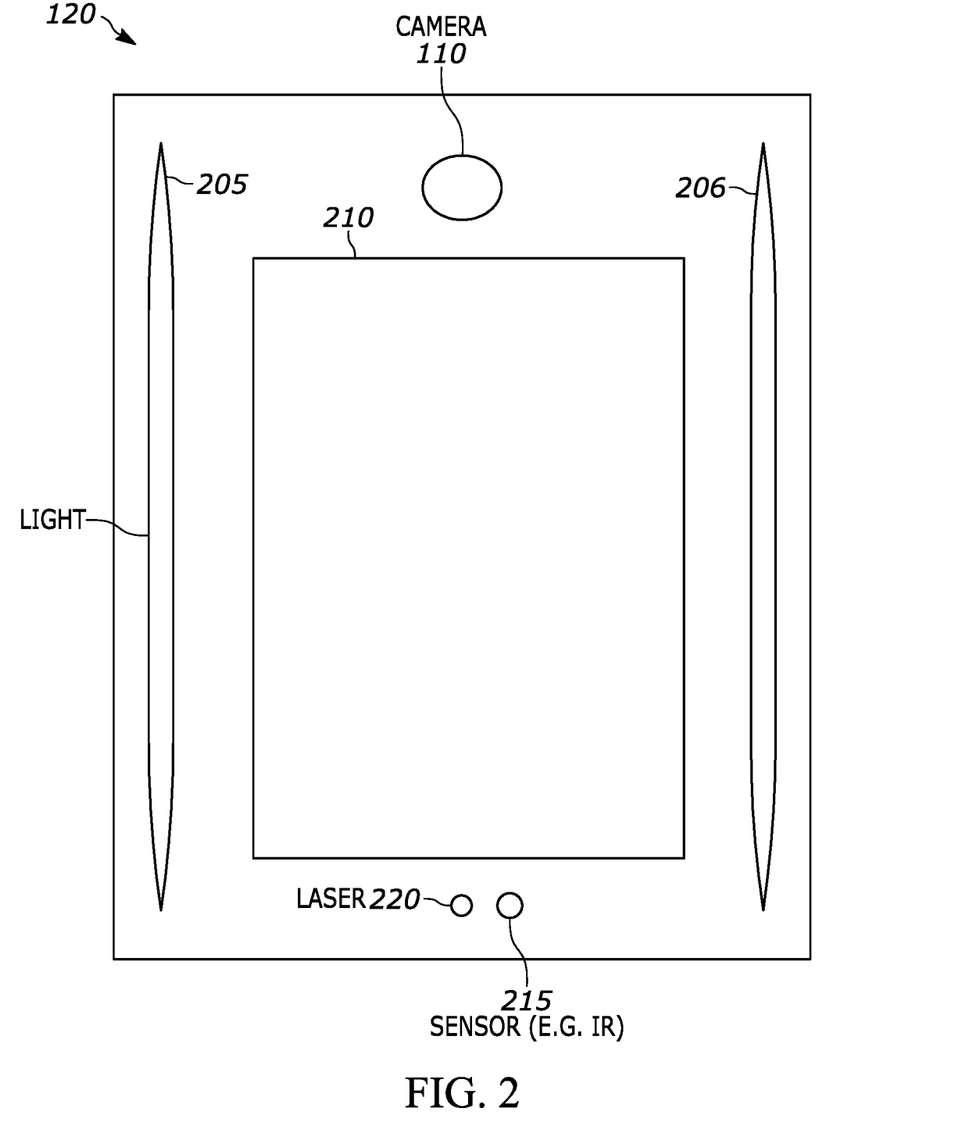
FIG. 2 illustrates a display apparatus according to one embodiment.

An example of the display 120 is illustrated in FIG. 2. The display 120 may include the camera 110, one or more lights 205-206, a primary display area 210, a sensor 215, and optionally at least one laser 220.

As described above, the camera 110 may be located behind the two-way mirror 115 and may be a component of the display 120. For example, if the display 120 is a tablet computer, the camera 110 may be an integrated camera of the tablet computer. The one or more lights 205-206 are configured to provide light for a dental professional who is examining the patient 105. In some embodiments, the one or more lights 205-206 are not components of the display 120, and the display 120 is instead configured to provide light to the patient 105 through the two-way mirror 115 as described below.

The primary display area 210 is used to display various informative graphics to the patient 105. The sensor 215 can be a variety of different sensors, for example, an ambient light sensor, IR sensor, LIDAR sensor, or other sensor. The at least one laser 220 is used to aid in detecting the patient 105 and positioning the patient 105. In embodiments where no laser is present, a line may instead be virtually drawn on the display 120 to aid in patient positioning and alignment. Each of these elements may be located behind the two-way mirror 115.

The display 120 can be operated in various modes in order to control what the patient 105 can see. A first mode is a mirror mode. The mirror mode is active when the display 120 is turned off or shows a low light intensity, dark background image. For example, the dark background image may be all-black, dark blue, dark brown, or another suitable dark color. Because the brightness of the display 120 is much less on the patient side surface 116 of the two-way mirror 115 than on the display side surface 117, the two-way mirror 115 acts as a regular mirror reflecting the face of the patient 105.

A second mode of the display 120 is a light mode. In the light mode, the display 120 outputs a high-intensity white image and the two-way mirror 115 transmits light from that image to the patient 105, allowing the display 120 to be used as a traditional lighting element by a dental professional.

A third mode of the display 120 is a monitor mode. In the monitor mode, the display 120 outputs captured images and is used as a normal monitor to provide information to the patient 105. For example, a video feed from the camera 110, dental information relevant to the patient 105, or other images or graphics are displayed on the display 120 when the display is in the monitor mode.

A fourth mode is of the display is an augmented mode. In the augmented mode, some portions of the display 120 output a low light intensity, all black background and other portions of the display 120 output high light intensity graphics. The two-way mirror 115 reflects the black background portions as if a regular mirror (e.g., allows the patient 105 to see their own face) and also allows the graphics to shine through and be visible to the patient 105. In this way, instructions, statistics, reports, text, and other graphics can be presented to the patient 105 while still reflecting the face of the patient 105. The graphics provide additional information augmented on top of the mirrored face of the patient 105.

Figure 3A:
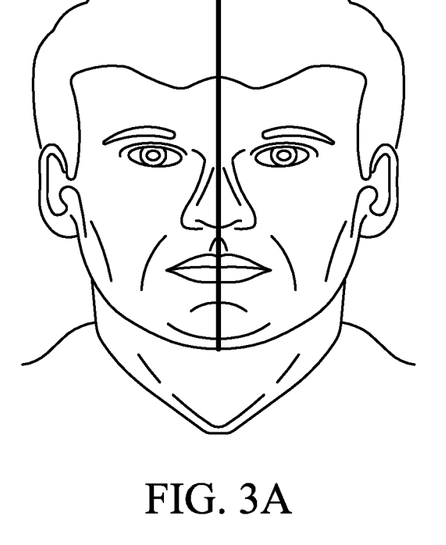
FIG. 3A illustrates a positioning guide including a mid-sagittal guide line overlaid on an image of a patient according to one embodiment.
Figure 3B:
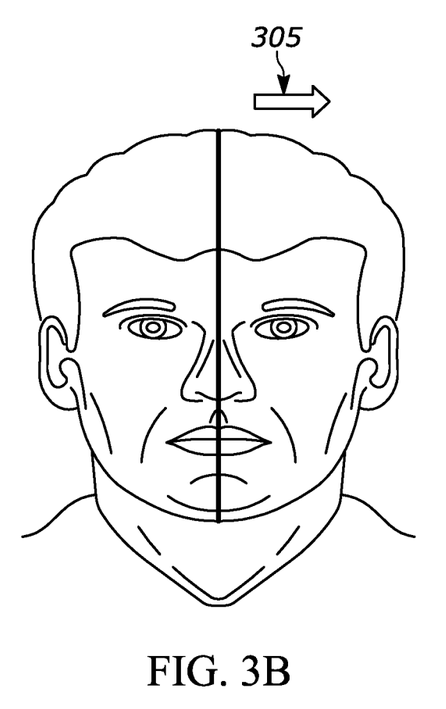
FIG. 3B illustrates a positioning guide including a mid-sagittal guide line overlaid on an image of a patient and a movement guide according to one embodiment.

In one embodiment, the display 120, when operating in the augmented mode, illustrates a positioning guide for the patient 105 to position themselves for x-ray image acquisition by the camera 110. The positioning guide may be, for example, a mid-sagittal vertical guide line, for example, the guide line found in FIG. 3A. The guide line is positioned over the reflected face of the patient 105 and provides a reference point for the patient 105 to align themselves for x-ray image acquisition by the camera 110. In other embodiments, a movement guide is provided along with the positioning guide. For example, FIG. 3B illustrates both a mid-sagittal vertical guide line and a movement guide 305 shown in this embodiment as an arrow shape. The movement guide 305 provides directions to the patient 105 in order to help align the patient 105 for scanning, for example, the movement guide 305 indicating for the patient 105 to move in the direction of the arrow to properly align the patient 105 for x-ray image acquisition.

Figure 4A:
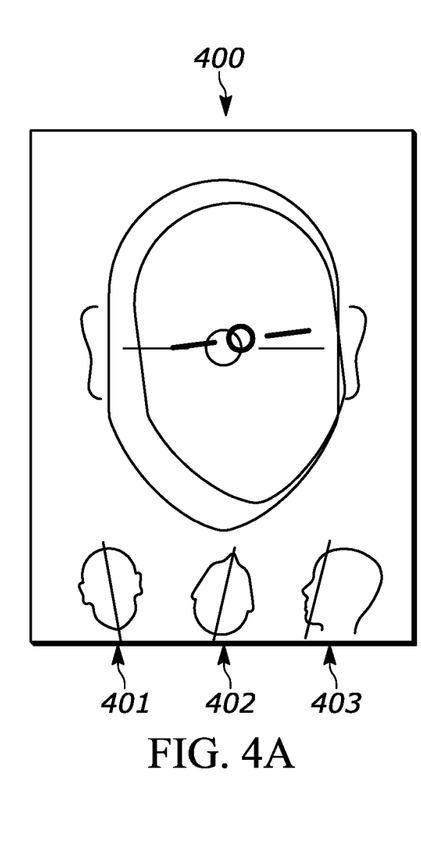
FIG. 4A illustrates a first instance of a positioning guide according to one embodiment.
Figure 4B:
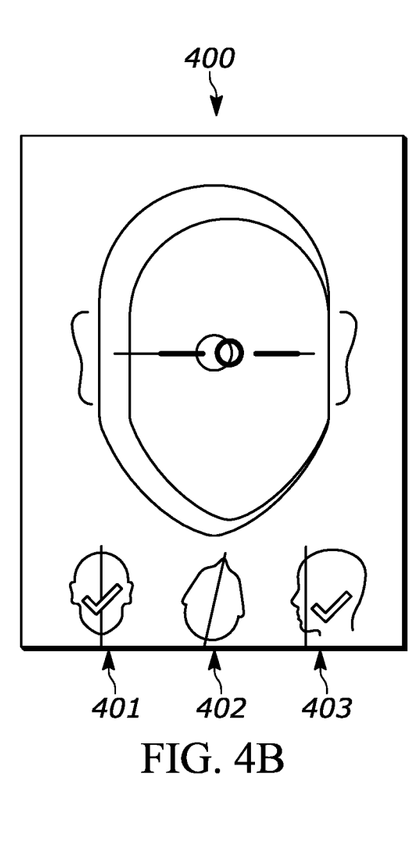
FIG. 4B illustrates a second instance of a positioning guide according to one embodiment.
Figure 4C:
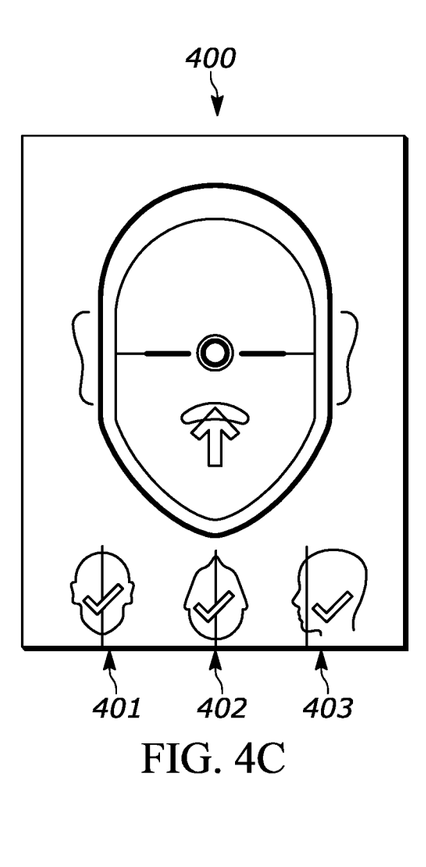
FIG. 4C illustrates a third instance of a positioning guide according to one embodiment.

The positioning guide and the movement guide (for example, the movement guide 305) may be more complex than a guide line and arrow. For example, FIGS. 4A-4C illustrate different instances of a positioning guide 400 according to one embodiment. Movement guides 401-403 illustrate different alignments of the head of the patient 105. For example, movement guide 401 illustrates an alignment of the head of the patient 105 in a first anatomical plane, movement guide 402 illustrates an alignment of the head of the patient 105 in a second anatomical plane, and movement guide 403 illustrates an alignment of the head of the patient 105 in a third anatomical plane. In embodiments with more cameras, more views of more anatomical planes can be captured.

To properly acquire images of the patient 105, the head of the patient 105 must be aligned in the first, second, and third anatomical planes. The movement guides 401-403 not only illustrate the current alignment of the head of the patient 105, but also provide indications to the patient 105 of proper or improper alignment. In order to determine proper or improper alignment, image data from the camera 110 is analyzed by the electronic processor 125 in order to determine patient position. For example, facial features of the patient 105 may be used to detect various relevant axes, for example, a Frankfort line, a back-front line, a feet-head line, and the like. Using later frames from the image data, an initial facial model can be registered and used to update the axes, allowing for the current orientation of the head or face of the patient 105 to be known.

For example, FIG. 4A illustrates a first instance of the positioning guide 400 indicating that the patient 105 is not in alignment. In addition to an outline of the head of the patient 105 providing real-time alignment information to the patient 105 in the positioning guide 400, the movement guides 401-403 indicate that the head of the patient 105 is out of alignment for each of the first, second, and third anatomical planes. This indication may be accomplished by displaying the movement guides 401 and 403 in a first color, for example, red, when the head of the patient 105 is out of alignment with the first and third anatomical planes, respectively. This indication may also be accomplished by displaying some other visual indication, for example, an "X" figure on the respective movement guide 401-403 where the head of the patient 105 is out of alignment. In other embodiments, audio directions may be given to the patient 105 based upon the alignment of the patient 105. In further embodiments, visual indications and audio directions may be used in tandem to position the patient 105.

FIG. 4B illustrates a second instance of the positioning guide 400. Based upon the outline provided by the positioning guide 400 illustrating the current alignment of the head of the patient 105, the patient 105 can reposition their head to move into alignment. As each of the first, second, and third anatomical planes of the head of the patient 105 are aligned, the movement guides 401-403 change dynamically to indicate to the patient 105 that the head is aligned in each plane. For example, in FIG. 4B, movement guides 401 and 403 change colors, stop displaying an alignment line, and display a check mark to indicate to the patient 105 that the head is aligned in the first and third anatomical planes. Portions of the positioning guide 400 may also be displayed in a different color or add or remove particular graphical elements when the head of the patient 105 is aligned in particular anatomical planes.

FIG. 4C illustrates a third instance of the positioning guide 400. In FIG. 4C, the movement guides 401-403 now all indicate that the head is properly aligned with each of the anatomical planes. Other portions of the positioning guide 400 may also change, for example, an outline of the positioning guide changing colors.

Figure 5:
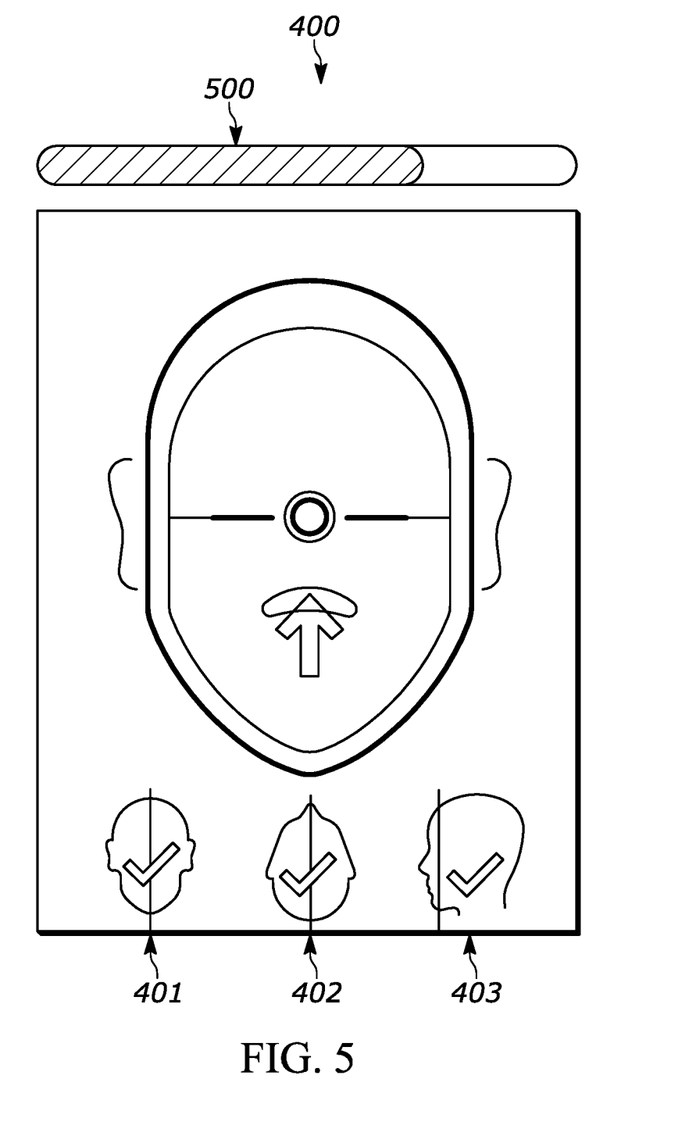
FIG. 5 illustrates a progress indicator and a positioning guide according to one embodiment.

Once the patient 105 is properly positioned, the x-ray image acquisition procedure can begin. To help maintain proper patient position, the display 120, in some embodiments, displays a progress indicator (in one example, a progress bar) in addition to the positioning guide 400. For example, FIG. 5 illustrates the positioning guide 400 being displayed along with a progress indicator 500. The progress indicator 500 indicates to the patient 105 how far along the x-ray image acquisition procedure is so that the patient 105 knows to maintain the proper position until the procedure is complete. By staying still during the procedure, motion artefacts are reduced. While the progress indicator 500 is illustrated as a progress bar in FIG. 5, the progress indicator may be any suitable graphic for indicating progress to the patient, for example, a spinning wheel, a text box showing a percentage of completion, or other method of showing progress.

In some embodiments, the display 120 is not coupled to the column of the X-ray imaging system 140. In some instances, it is connected or coupled to other components of the X-ray imaging system 140. In still other embodiments, the display 120 is located near the X-ray imaging system 140, for example, in the same room, and is communicatively coupled to the X-ray imaging system 140. In these embodiments, instead of providing directions to the patient 105 through the two-way mirror 115 with the display 120, the camera 110 captures images of the face of the patient 105 and a second user, such as a nurse, dentist, dental hygienist, or other operator, views the captured images from the camera 110 on the display 120 and provides instructions to the patient 105 to properly position for an x-ray imaging procedure. Much like the movement guides 401-403 described above, the second user of the display 120 can see displayed movement guides on the display 120 and provide instructions to the patient 105 for positioning based on the displayed movement guides.

Returning to FIG. 1A, the electronic processor 125 is electronically connected to the display 120 and the camera 110 and, among other functions, controls the operation of the display 120 and the camera 110. The electronic processor 125 may be a programmable electronic microprocessor, a microcontroller, an application-specific integrated circuit ("ASIC"), or a similar device. The electronic processor 125 may be implemented in several independent processors (for example, programmable electronic control units) each configured to perform specific functions or sub-functions. Additionally, the electronic processor may contain sub-modules configured to handle input/output functions, processing of signals, and application of the methods described herein.

The electronic processor 125 is also communicatively coupled to the non-transitory, computer-readable medium 130 and the human-machine interface 135. The electronic processor 125 is configured to retrieve data from the non-transitory, computer-readable medium 130 and execute, among other things, software related to the processes and methods described herein.

The human-machine interface 135 includes an input device, an output device, or a combination thereof. For example, the human-machine interface 135 may include a display device separate from the display 120, a touchscreen, a keyboard, a keypad, a button, a cursor-control device, a printer, a speaker, a virtual reality headset, a microphone, and the like. In some embodiments, the system 100 includes multiple human-machine interfaces. For example, the system 100 may include a touchscreen and a keypad. In some embodiments, the human-machine interface 135 is included in the same housing as the electronic processor 125. However, in other embodiments, the human-machine interface 135 may be external to the electronic processor 125 but communicates with the electronic processor 125 over a wired or wireless connection. As described herein, one or more human-machine interfaces 135 receive input from a user, which the electronic processor 125 uses to control the system 100.

Figure 6:
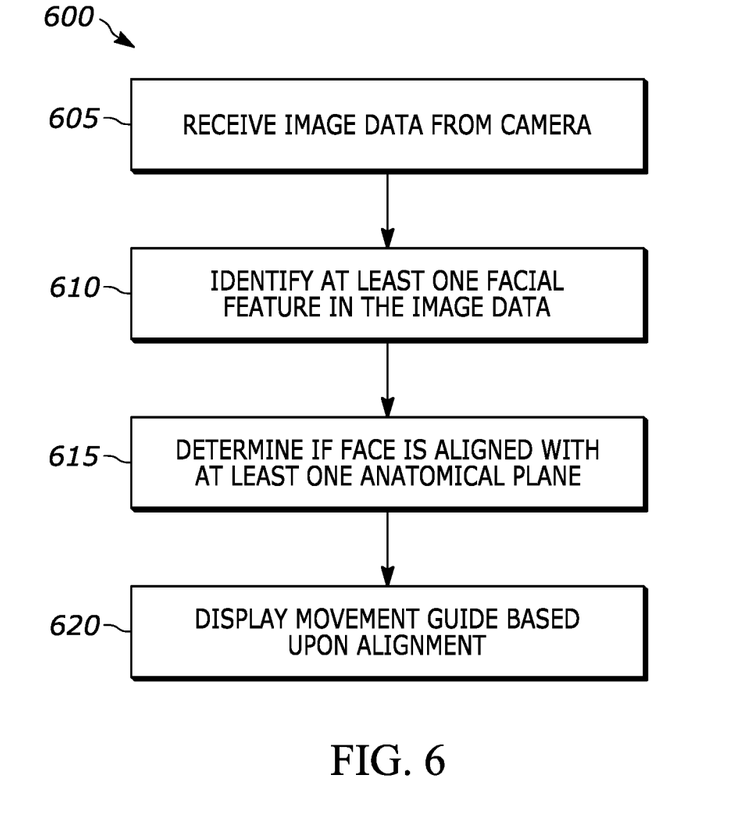
FIG. 6 is a flow chart illustrating a method of positioning a patient for x-ray image acquisition according to one embodiment.

FIG. 6 illustrates a flow chart of a method 600 for positioning the patient 105 for x-ray image acquisition according to one embodiment. The method 600 includes receiving, with the electronic processor 125, image data from the camera 110 (at block 605). The image data may be still images or video data. The image data includes images of the face of the patient 105.

Based upon the received image data, the electronic processor 125 identifies at least one facial feature of the patient 105 (at block 610). For example, as described above, relevant axes, for example, a Frankfort line, a back-front line, or a feet-head line can be identified using facial features in a coordinate system of the camera 110. Additional image data is then used to register an initial model. Based upon a difference between an initial frame of the image data and a current frame of the image data, relevant axes can be updated and a current orientation of the head of the patient 105 can be determined. In another example, instead of using a difference between an initial frame and a current frame of image data, continuous landmark detection (for example, tracking an eye, nose, mouth, or other facial feature) can be used to obtain a current orientation of the head of the patient 105.

Using the current orientation of the head of the patient 105, the electronic processor 125 can determine if the face of the patient is aligned with at least one anatomical plane (at block 615). For example, as described above, the current orientation of the head may be compared to a mid-sagittal plane, a coronal plane, and others. Based upon the type of x-ray image acquisition being performed, the patient 105 must be aligned with a variety of combinations of anatomical planes. The current orientation of the head is compared to the desired combination of anatomical planes for alignment.

If the current orientation of the head is aligned with all of the desired anatomical planes, the electronic processor 125 is configured to display an indication to the patient 105 using movement guides with alignment indicators showing the patient 105 that they are aligned (at block 620). For example, FIG. 4C illustrates this condition. If the current orientation of the head is out of alignment with one or more anatomical planes, the electronic processor 125 instead displays movement guides illustrating the current orientation of the head with respect to the various anatomical planes, allowing the patient 105 to see where their head is out of alignment and correct for it. This condition is illustrated in FIG. 4A.

If the patient is aligned with the various anatomical planes, the electronic processor 125 is configured to begin x-ray image acquisition and may also display a progress indicator to the patient 105. The progress indicator indicates how complete x-ray image acquisition is, which provides a visual reference to the patient 105 indicating how long they must hold the current aligned position. Once the progress indicator is complete, the patient 105 may move again. The progress indicator may also be displayed on a portion of the display 120 such that it can be used as a focus point for the patient 105 to maintain the proper alignment. This portion of the display 120 may be determined by the electronic processor 125 before or after alignment is determined.

The following examples illustrate example systems and methods described herein. Example 1: a dental x-ray image acquisition system, the system comprising at least one camera configured to capture an image of a patient, a display configured to display an image, a two-way mirror positioned in between a patient location and the display, and an electronic processor coupled to the camera and the display, the electronic processor configured to control the display and the camera.

Example 2: the dental x-ray image acquisition system of example 1, wherein the two-way mirror is also positioned between the camera and the patient.

Example 3: the dental x-ray image acquisition system any of examples 1-2, wherein the camera is a component of the display.

Example 4: the dental x-ray image acquisition system of example 1, wherein the camera is a three-dimensional camera.

Example 5: a dental x-ray image acquisition system, the system comprising at least one camera configured to capture an image of a patient, a display, a two-way mirror positioned in between a patient location and the display, and an electronic processor coupled to the camera and the display, the electronic processor configured to select, based upon a user input, an operating mode for the display and, based upon the selected operating mode, display at least one image on the display.

Example 6: the system of example 5, wherein the operating mode is an operating mode selected from a group of operating modes consisting of a mirror mode, an augmented mode, a light mode, and a monitor mode.

Example 7: the system of example 6, wherein the mirror mode consists of the display displaying a low intensity, dark background image.

Example 8: the system of example 6, wherein the augmented mode consists of the display displaying a low intensity, dark background image in a first portion of the display and displaying at least one other image in a second portion of the display.

Example 9: the system of example 8, wherein the at least one other image displayed on the display is a positioning guide for the patient.

Example 10: the system of example 9, wherein the positioning guide illustrates at least one movement guide for the patient.

Example 11: the system according to example 10, wherein the movement guide illustrates a direction of movement for the patient.

Example 12: the system of any of examples 10-11, wherein the movement guide illustrates an alignment of a head of the patient with respect to at least one anatomical plane.

Example 13: the system of example 12, wherein the movement guide illustrates alignment of the head of the patient with respect to two or more anatomical planes.

Example 14: the system of any of examples 12-13, wherein a graphical element of the movement guide is changed when the head of the patient is aligned with the at least one anatomical plane.

Example 15: a method for positioning a patient for x-ray image acquisition, the method comprising receiving, with an electronic processor, image data from at least one camera; identifying, with the electronic processor, at least one facial feature of the patient in the image data; determining, with the electronic processor, if a face of the patient is aligned with at least one anatomical plane based upon the at least one facial feature; and displaying, with the electronic processor, at least one movement guide on a display based upon the determined alignment of the face of the patient.

Example 16: the method of example 15, wherein the movement guide includes an indicator that the face of the patient is aligned with the at least one anatomical plane.

Example 17: the method of example 16, further comprising displaying, with the electronic processor, a progress indicator indicating to the patient to maintain a current position for a duration of image acquisition.

Example 18: the method of example 15, wherein the movement guide includes an indicator that the face of the patient is not aligned with the at least one anatomical plane.

Example 19: the method of any of examples 15-18, wherein at least one axis is detected using the at least one facial feature.

Example 20: the method of example 19, wherein a current orientation of the face of the patient is determined using the at least one axis.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms, for example, first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized electronic processors (or "processing devices"), for example, microprocessors, digital signal processors, customized processors and field programmable gate arrays (FPGAs) and unique stored program instructions (including both software and firmware) that control the one or more electronic processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (for example, comprising an electronic processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A dental x-ray image acquisition system, the system comprising:
    at least one camera configured to capture an image of a patient;
    a display configured to display an image;
    a two-way mirror positioned in between a patient location and the display; and
    an electronic processor coupled to the camera and the display, the electronic processor configured to control the display and the camera.

2. The dental x-ray image acquisition system of claim 1, wherein the two-way mirror is also positioned between the camera and the patient.

3. The dental x-ray image acquisition system of claim 1, wherein the camera is a component of the display.

4. The dental x-ray image acquisition system of claim 1, wherein the camera is a three-dimensional camera.

5. A dental x-ray image acquisition system, the system comprising:
    at least one camera configured to capture an image of a patient;
    a display;
    a two-way mirror positioned in between a patient location and the display; and
    an electronic processor coupled to the camera and the display, the electronic processor configured to
        select, based upon a user input, an operating mode for the display; and
        based upon the selected operating mode, display at least one image on the display.

6. The system of claim 5, wherein the operating mode is an operating mode selected from a group of operating modes consisting of a mirror mode, an augmented mode, a light mode, and a monitor mode.

7. The system of claim 6, wherein the mirror mode consists of the display displaying a low intensity, dark background image.

8. The system of claim 6, wherein the augmented mode consists of the display displaying a low intensity, dark background image in a first portion of the display and displaying at least one other image in a second portion of the display.

9. The system of claim 8, wherein the at least one other image displayed on the display is a positioning guide for the patient.

10. The system of claim 9, wherein the positioning guide illustrates at least one movement guide for the patient.

11. The system according to claim 10, wherein the movement guide illustrates a direction of movement for the patient.

12. The system of claim 10, wherein the movement guide illustrates an alignment of a head of the patient with respect to at least one anatomical plane.

13. The system of claim 12, wherein the movement guide illustrates alignment of the head of the patient with respect to two or more anatomical planes.

14. The system of claim 12, wherein a graphical element of the movement guide is changed when the head of the patient is aligned with the at least one anatomical plane.

* * * * *